(12) United States Patent
Inanaga et al.

(10) Patent No.: US 6,274,745 B1
(45) Date of Patent: Aug. 14, 2001

(54) BINAPHTHOL MONOPHOSPHORIC ACID DERIVATIVE AND ITS USE

(75) Inventors: Junji Inanaga; Hiroshi Furuno, both of Fukuoka (JP)

(73) Assignee: Tosoh Corporation, Yamaguchi-ken (JP)

( * ) Notice: Subject to any disclaimer, the term of this patent is extended or adjusted under 35 U.S.C. 154(b) by 0 days.

(21) Appl. No.: 09/533,069

(22) Filed: Mar. 22, 2000

(30) Foreign Application Priority Data

Mar. 24, 1999 (JP) .................................. 11-079433

(51) Int. Cl.⁷ .......................... C07D 315/00; C07F 9/141
(52) U.S. Cl. ............................ 549/416; 549/356; 549/28; 558/73; 558/83; 562/19
(58) Field of Search .................... 549/416, 200, 549/13, 28, 425, 356; 558/73, 83; 562/19

(56) References Cited

U.S. PATENT DOCUMENTS 3,848,030   11/1974   Viterbo et al. .
5,767,295 *  6/1998   Mitsuda et al. ..................... 549/425

FOREIGN PATENT DOCUMENTS 2212660    9/1972   (DE) .

OTHER PUBLICATIONS

CA:89:109618 abs of US4043979, Aug. 1977.*
CA:88:190784 abs of J Org Chem by Cram et al 43(10) pp. 1930–46, 1978.*
CA:131:175559 abs of Kidorui by Furuno et al 34, pp. 306–307, 1999.*
Hanamoto et al, "Asymmetric Hetero Diels–Alder Reaction . . . " Synlett, 1/97, pp. 79–80.
Inanaga et al, "Achiral and Chiral Lanthanide (III) Salts Of Superacids . . . " New J. Chem vol. 19 (5–6), 1995, pp. 707–712.
Maruoka et al, "Asymmetric Hetero– Diels–Alder Reaction Catalyzed . . . " J. Am. Chem. Soc. vol. 110, 1988 No. 1, 1/88, pp. 310–312.
Hiroshi et al, "Synthesis of Novel Rare Earth Metal . . . " Chemical Abstracts vol. 131 No. 13, 9/99, p. 1160.

* cited by examiner

Primary Examiner—Jean F. Vollano
(74) Attorney, Agent, or Firm—Nixon & Vanderhye

(57) ABSTRACT

A binaphthol monophosphoric acid derivative of the following formula (1), (2), (3) or (4):

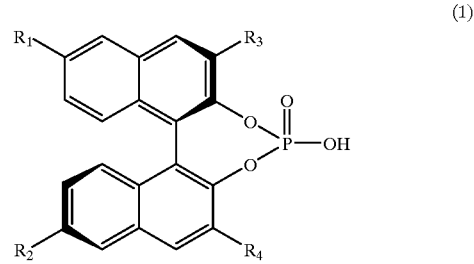

(1)

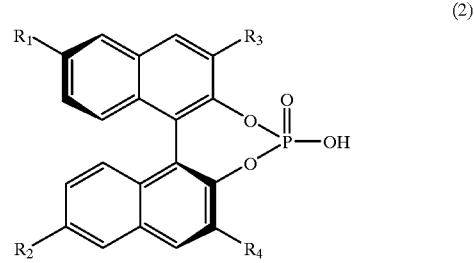

(2)

wherein each of $R_1$, $R_2$, $R_3$ and $R_4$ which are independent of one another, is hydrogen, a $C_{2-20}$ linear or branched alkenyl group, a $C_{2-20}$ linear or branched alkynyl group, a phenyl group, a phenyl group having its nucleus substituted at the 1- to 4-carbon atom by a $C_{1-10}$ linear or branched alkyl group, a phenyl group having its nucleus substituted at the 1- to 4-carbon atom by a $C_{2-10}$ linear or branched alkenyl group, a phenyl group having its nucleus substituted at the 1- to 4-carbon atom by a $C_{2-10}$ linear or branched alkynyl group, a naphthyl group or a $C_{3-8}$ cycloalkyl group, provided that $R_1$ to $R_4$ are not simultaneously hydrogen,

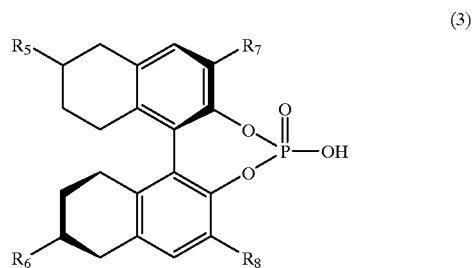

(3)

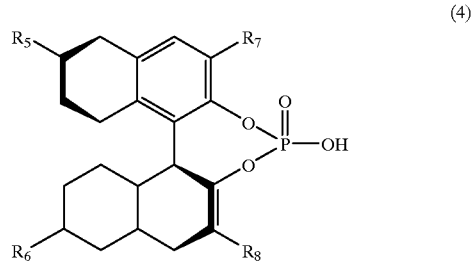

(4)

wherein each of $R_5$, $R_6$, $R_7$ and $R_8$ which are independent of one another, essentially the same as $R_1$, $R_2$, $R_3$ and $R_4$.

4 Claims, No Drawings

BINAPHTHOL MONOPHOSPHORIC ACID DERIVATIVE AND ITS USE

BACKGROUND OF THE INVENTION

1. Field of the Invention

The present invention relates to optically active binaphthol monophosphoric acid derivatives, optically active binaphthol monophosphate derivatives and their use. The optically active binaphthol monophosphate acid derivatives of the present invention are important as in intermediates for synthesis of various catalysts for asymmetric synthesis, and the binaphthol monophosphate derivatives derived therefrom have high reactivity in various asymmetric synthetic reactions and provide reaction products having a high optical purity. Pyran compounds obtained by the method of the present invention are useful compounds as intermediates for synthesis of pharmaceutical and agricultural chemicals.

2. Discussion of Background

The binaphthol monophosphoric acid derivatives of the present invention and the binaphthol monophosphate derivatives derived therefrom, have not been conventionally known, and they are novel compounds.

As one example of reactions to which the catalyst for asymmetric synthesis of the present invention is applicable, Diels-Alder cyclization reaction will be explained below.

As the Diels-Alder cyclization reaction, many reactions of a diene with an olefin in the presence or absence of a Lewis acid catalyst such as aluminum chloride, have been known for a long time.

As an asymmetric Diels-Alder cyclization reaction, e.g. a reaction of acryl-1,3-oxazolidin-2-one with cyclopentadiene has been known (Shu Kobayashi et al, J. Org. Chem., 1994, 59, 3758).

As an asymmetric hetero Diels-Alder cyclization reaction, e.g. a reaction of a benzaldehyde with a diene has been known (Hisashi Yamamoto et al, J. Am. Chem. 1988, 110, 310).

However, with respect to the conventional asymmetric Diels-Alder cyclization reactions and asymmetric hetero Diels-Alder cyclization reactions, the reaction temperature is as low as at most −20° C. in all known reactions, whereby these reactions are not satisfactory as an industrial production method, although a reaction product having a high optical purity may be obtained in some of these reactions.

SUMMARY OF THE INVENTION

The present invention has been made to overcome the above object, and it is an object of the present invention to provide a novel binaphthol monophosphate derivative useful as a catalyst for asymmetric synthesis which can be used under more practical reaction conditions and which provides a high optical purity, and its intermediate binaphthol monophosphoric acid derivative.

The present inventors have conducted extensive studies to develop a catalyst for asymmetric synthesis which can be used under more practical reaction conditions and which provides a high optical purity, and as a result, they have found a binaphthol monophosphoric acid derivative of the following formula (1) or (2):

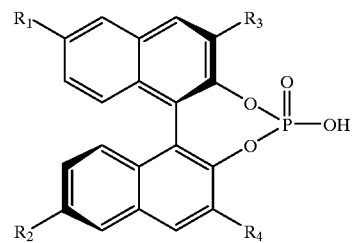

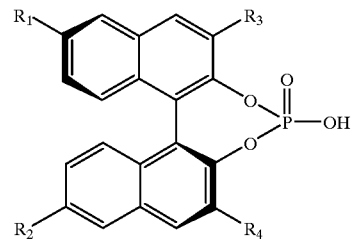

wherein each of $R_1$, $R_2$, $R_3$ and $R_4$ which are independent of one another, is hydrogen, a $C_{1-20}$ linear or branched alkyl group, a $C_{2-20}$ linear or branched alkenyl group, a $C_{2-20}$ linear or branched alkynyl group, a phenyl group, a phenyl group having its nucleus substituted at the 1- to 4-carbon atom by a $C_{1-10}$ linear or branched alkyl group, a phenyl group having its nucleus substituted at the 1- to 4-carbon atom by a $C_{2-10}$ linear or branched alkenyl group, a phenyl group having its nucleus substituted at the 1- to 4-carbon atom by a $C_{2-10}$ linear or branched alkynyl group, a naphthyl group or a $C_{3-8}$ cycloalkyl group, provided that $R_1$ to $R_4$ are not simultaneously hydrogen; and a novel binaphthol monophosphoric acid derivative of the following formula (3) or (4) derived from a known compound:

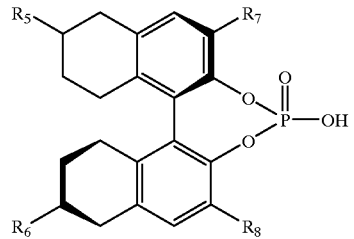

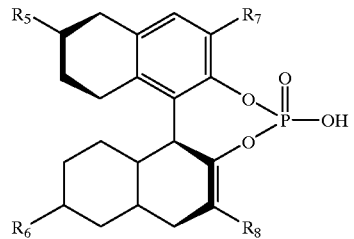

wherein each of $R_5$, $R_6$, $R_7$ and $R_8$ which are independent of one another, is hydrogen, a $C_{1-20}$ linear or branched alkyl group, a $C_{1-20}$ linear or branched alkenyl group, a $C_{2-20}$ linear or branched alkynyl group, a phenyl group, a phenyl group having its nucleus substituted at the 1- to 4-carbon atom by a $C_{1-10}$ linear or branched alkyl group, a phenyl group having its nucleus substituted at the 1- to 4-carbon atom by a $C_{2-10}$ linear or branched alkenyl group, a phenyl group having its nucleus substituted at the 1- to 4-carbon atom by a $C_{2-10}$ linear or branched alkynyl group, a naphthyl group or a $C_{3-8}$ cycloalkyl group. Further, they have found a binaphthol monophosphate derivative of the following formula (5), (6), (7) or (8):

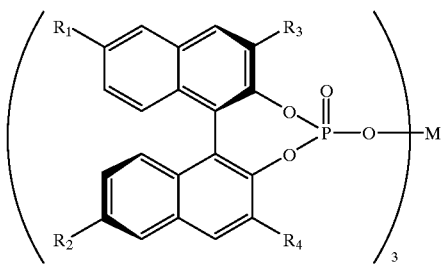

(5)

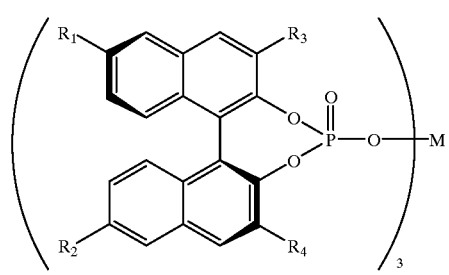

(6)

wherein each of $R_1$, $R_2$, $R_3$ and $R_4$ which are independent of one another, is hydrogen, a $C_{1-20}$ linear or branched alkyl group, a $C_{2-20}$ linear or branched alkenyl group, a $C_{2-20}$ linear or branched alkynyl group, a phenyl group, a phenyl group having its nucleus substituted at the 1- to 4-carbon atom by a $C_{1-10}$ linear or branched alkyl group, a a phenyl group having its nucleus substituted at the 1- to 4-carbon atom by a $C_{2-10}$ linear or branched alkenyl group, a phenyl group having its nucleus substituted at the 1- to 4-carbon atom by a $C_{2-10}$ linear or branched alkynyl group, a naphthyl group or a $C_{3-8}$ cycloalkyl group, provided that $R_1$ to $R_4$ are not simultaneously hydrogen, and M is a metal element capable of forming a trivalent metal ion,

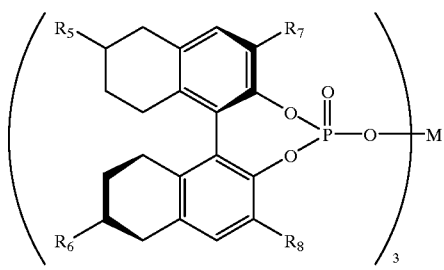

(7)

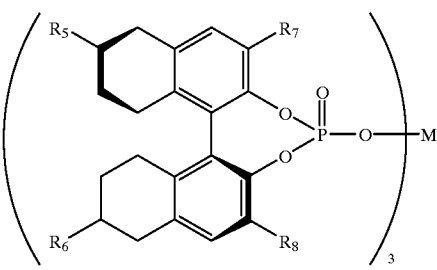

(8)

wherein each of $R_5$, $R_6$, $R_7$ and $R_8$ which are independent of one another, is hydrogen, a $C_{1-20}$ linear or branched alkyl group, a $C_{2-20}$ linear or branched alkenyl group, a $C_{2-20}$ linear or branched alkynyl group, a phenyl group, a phenyl group having its nucleus substituted at the 1- to 4-carbon atom by a $C_{1-10}$ linear or branched alkyl group, a phenyl group having its nucleus substituted at the 1- to 4-carbon atom by a $C_{2-10}$ linear or branched alkenyl group, a phenyl group having its nucleus substituted at the 1- to 4-carbon atom by a $C_{2-10}$ linear or branched alkynyl group, a naphthyl group or a $C_{3-8}$ cycloalkyl group, and M is a metal element capable of forming a trivalent metal ion; which is useful as a catalyst for asymmetric synthesis, and which is derived from the compound of the above formula (1), (2), (3) or (4). They have found that when the binaphthol monophosphate derivative is applied to an asymmetric hetero Diels-Alder cyclization reaction, the reaction can be carried out at room temperature, and the desired compound having a high optical purity can be obtained. The present invention has been accomplished on the basis of these discoveries.

Namely, the present invention provides binaphthol monophosphoric acid derivatives of the above formulae (1) to (4), binaphthol monophosphate derivatives of the above formulae (5) to (8), and their use.

DETAILED DESCRIPTION OF THE PREFERRED EMBODIMENTS

The binaphthol monophosphoric acid derivatives of the above formulae (1) to (4) of the present invention, can be derived from optically active (R) or (S) binaphthol as the starting material, in several steps.

For example, the binaphthol monophosphoric acid derivative of the above formula (1) or (2) of the present invention may be obtained in accordance with e.g. methods as described in Reference Examples and Examples of the present invention, in such a manner that a commercially available optically active (R) or (S) 1,1'-binaphthyl-2,2'-diol is used as the starting material, the diol is protected, then, the starting material is converted to a halide at the 3,3'-positions and/or a halide at the 6,6'-positions, a substituent is introduced by e.g. a cross-coupling reaction, followed by a reaction with e.g. phosphorus oxychloride to obtain the binaphthol monophosphoric acid derivative of the formula (1) or (2).

Likewise, the binaphthol monophosphoric acid derivative of the above formula (3) or (4) may be obtained by using, as the starting material, commercially available optically active (R) or (S) 1,1'-binaphthyl-2,2'-diol or binaphthol derivatives obtained as an intermediate for synthesis of the binaphthol monophosphoric acid of the above formula (1) or (2), carrying out partial hydrogenation reaction in accordance with a known method (D. J. Cram, et al., J. Org. Chem., 1978, 43, 1930) to obtain a 5,6,7,8,5',6',7',8'-octahydro-1,1'-binaphthyl-2,2'-diol derivative, and reacting said diol derivative as the starting material with e.g. phosphorus oxychloride.

Further, the binaphthol monophosphate derivatives of the above formulae (5) to (8) of the present invention may be prepared by reacting the binaphthol monophosphoric acid derivatives of the above formulae (1) to (4) with a trivalent metal salt.

Specific examples of the binaphthol monophosphoric acid derivative of the present invention include (R)-(−)-5,6,7,8,5',6',7',8'-octahydro-1,1'-binaphthyl-2,2'-diyl phosphoric acid, (S)-(+)-5,6,7,8,5',6',7',8'-octahydro-1,1'-binaphthyl-2,2'-diyl phosphoric acid, (R)-(−)-6,6'-dimethyl-1,1'-binaphthyl-2,2'-diyl phosphoric acid, (S)-(+)-6,6'-dimethyl-1,1'-binaphthyl-2,2'-diyl phosphoric acid, (R)-(−)-6,6'-diethyl-1,1'-binaphthyl-2,2'-diyl phosphoric acid, (S)-(+)-6,6'-diethyl-1,1'-binaphthyl-2,2'-diyl phosphoric acid, (R)-(−)-6,6'-di-n-propyl-1,1'-binaphthyl-2,2'-diyl phosphoric acid, (S)-(+)-6,6'-di-n-propyl-1,1'-binaphthyl-2,2'-diyl phosphoric acid, (R)-(−)-6,6'-diisopropyl-1,1'-binaphthyl-2,2'-diyl phosphoric acid, (S)-(+)-6,6'-diisopropyl-1,1'-binaphthyl-2,2'-diyl phosphoric acid, (R)-(−)-6,61-di-n-butyl-1,1'-binaphthyl-2,2'-diyl phosphoric acid, (S)-(+)-6,6'-di-n-butyl-1,1'-binaphthyl-2,2'-diyl phosphoric acid, (R)-(−)-6,6'-di-tert-butyl-1,1'-binaphthyl-2,2'-diyl phosphoric acid, (S)-(+)-6,6'-di-tert-butyl-1,1'-binaphthyl-2,2'-diyl phosphoric acid, (R)-(−)-6,6'-di-n-pentyl-1,1 '-binaphthyl-2,2'-diyl phosphoric acid, (S)-(+)-6,6'-di-n-pentyl-1,1'-binaphthyl-2,2'-diyl phosphoric acid, (R)-(−)-6,6'-di-n-hexyl-1,1'-binaphthyl-2,2'-diyl phosphoric acid, (S)-(+)-6,6'-di-n-hexyl-1,1'-binaphthyl-2,2'-diyl phosphoric acid, (R)-(−)-6,6'-dicyclohexyl-1,1'-binaphthyl-2,2'-diyl phosphoric acid, (S)-(+)-6,6'-dicyclohexyl-1,1'-binaphthyl-2,2'-diyl phosphoric acid, (R)-(−)-6,6'-di-n-heptyl-1,1'-binaphthyl-2,2'-diyl phosphoric acid, (S)-(+)-6,6'-di-n-heptyl-1,1'-binaphthyl-2,2'-diyl phosphoric acid, (R)-(−)-6,6'-di-n-octyl-1,1'-binaphthyl-2,2'-diyl phosphoric acid, (S)-(+)-6,6'-di-n-octyl-1,1'-binaphthyl-2,2'-diyl phosphoric acid, (R)-(−)-6,6'-di-n-nonyl-1,1'-binaphthyl-2,2'-diyl phosphoric acid, (S)-(+)-6,6'-di-n-nonyl-1,1'-binaphthyl-2,2'-diyl phosphoric acid, (R)-(−)-6,6'-di-n-decyl-1,1'-binaphthyl-2,2'-diyl phosphoric acid, (S)-(+)-6,6'-di-n-decyl-1,1'-binaphthyl-2,2'-diyl phosphoric acid, (R)-(−)-6,6'-diphenyl 1,1'-binaphthyl-2,2'-diyl phosphoric acid, (S)-(+)-6,6'-diphenyl 1,1'-binaphthyl-2,2'-diyl phosphoric acid, (R)-(−)-6,6'-bis(4-methylphenyl)-1,1'-binaphthyl-2,2'-diyl phosphoric acid, (S)-(+)-6,6'-bis(4-methylphenyl)-1,1'-binaphthyl-2,2'-diyl phosphoric acid, (R)-(−)-6,6'-bis(2,6-dimethylphenyl)-1,1'-binaphthyl-2,2'-diyl phosphoric acid, (S)-(+)-6,6'-bis(2,6-dimethylphenyl)-1,1'-binaphthyl-2,2'-diyl phosphoric acid, (R)-(−)-3,3'-diethynyl-1,1'-binaphthyl-2,2'-diyl phosphoric acid, (S)-(+)-3,3'-diethynyl-1,1 '-binaphthyl-2,2'-diyl phosphoric acid, (R)-(−)-6,6'-diethenyl-1,1'-binaphthyl-2,2'-diyl phosphoric acid, (S)-(+)-6,6'-diethenyl-1,1'-binaphthyl-2,2'-diyl phosphoric acid, (R)-(−)-6,6'-di(1"-octenyl)-1,1'-binaphthyl-2,2'-diyl phosphoric acid, (S)-(+)-6,6'-di(1"-octenyl)-1,1'-binaphthyl-2,21-diyl phosphoric acid, (R)-(−)-6,6'-diethynyl-1,1'-binaphthyl-2,2'-diyl phosphoric acid, (S)-(+)-6,6'-diethynyl-1,1'-binaphthyl-2,2'-diyl phosphoric acid, (R)-(−)-3,3'-diethynyl-1,1'-binaphthyl-2,2'-diyl phosphoric acid, (S)-(+)-3,3$^1$-diethynyl-1,1'-binaphthyl-2,2'-diyl phosphoric acid, (R)-(−)-3,3'-diethenyl-1,1'-binaphthyl-2,2'-diyl phosphoric acid and (S)-(+)-3,3'-diethenyl-1,1'-binaphthyl-2,2'-diyl phosphoric acid. These phosphoric acid derivatives include one having from 0 to 10 molecules of water of crystallization when isolated as a crystal.

The catalyst of the present invention comprises the binaphthol monophosphate derivative of the above formula (5), (6), (7) or (8).

In the binaphthol monophosphate derivatives of the above formulae (5) to (8), the salt-forming metal element may be any metal element capable of stably forming a trivalent metal salt, it is preferably a lanthanum series element, and specifically, an element selected from the group consisting of scandium, yttrium, lanthanum, cerium, praseodymium, neodymium, samarium, europium, gadolinium, terbium, dysprosium, holmium, erbium, thulium, ytterbium and lutetium, may, for example, be mentioned.

The catalyst of the present invention may be any one comprising the binaphthol monophosphate derivative of the above formula (5), (6), (7) or (8), and is not particularly limited. Specific examples of the catalyst include gadolinium tris[(R)-(−)-6,6'-di-n-octyl-1,1'-binaphthyl-2,2'-diyl phosphate], gadolinium tris[(S)-(+)-6,6'-di-n-octyl-1,1'-binaphthyl-2,2'-diyl phosphate], gadolinium tris[(R)-(−)-6,6'-di-n-octenyl-1,1'-binaphthyl-2,2'-diyl phosphate], gadolinium tris[(S)-(+)-6,6'-di-n-octenyl-1,1'-binaphthyl-2,2'-diyl phosphate], ytterbium tris[(R)-(−)-6,6'-di-n-octyl-1,1'-binaphthyl-2,2'-diyl phosphate], ytterbium tris[(S)-(+)-6,6'-di-n-octyl-1,1'-binaphthyl-2,2'-diyl phosphate], scandium tris[(R)-(−)-6,6'-di-n-octyl-1,1'-binaphthyl-2,2'-diyl phosphate], scandium tris[(S)-(+)-6,6'-di-n-octyl-1,1'-binaphthyl-2,2'-diyl phosphate], gadolinium tris[(R)-(−)-6,6'-di(2",6"-dimethylphenyl)-1,1'-binaphthyl-2,2'-diyl phosphate], gadolinium tris[(S)-(+)-6,6'-di(2",6"-dimethylphenyl)-1,1'-binaphthyl-2,2'-diyl phosphate], ytterbium tris[(R)-(−)-6,6'-di(20, 6"-dimethylphenyl)-1,1'-binaphthyl-2,2'-diyl phosphate], ytterbium tris[(S)-(+)-6,6'-di(2",6"-dimethylphenyl)-1,1'-binaphthyl-2,2'-diyl phosphate], scandium tris[(R)-(−)-6,6'-di(2",6"-dimethylphenyl)-1,1'-binaphthyl-2,2'-diyl phosphate], scandium tris[(S)-(+)-6,6'-di(2",6"-dimethylphenyl)-1,1'-binaphthyl-2,2'-diyl phosphate], gadolinium tris[(R)-(−)-5,6,7,8,5',6',7',8'-octahydro-1,1'-binaphthyl-2,2'-diyl phosphate], gadolinium tris[(S)-(+)-5,6,7,8,5',6',7',8'-octahydro-1,1'-binaphthyl-2,2'-diyl phosphate], ytterbium tris[(R)-(−)-5,6,7,8,5',6',7',8'-octahydro-1,1'-binaphthyl-2,2'-diyl phosphate], ytterbium tris[(S)-(+)-5,6,7,8,5',6',7',8'-octahydro-1,1'-binaphthyl-2,2'-diyl phosphate], scandium tris[(R)-(−)-5,6,7,8,5',6'7',8'-octahydro-1,1'-binaphthyl-2,2'-diyl phosphate], scandium tris[(S)-(+)-5,6,7,8,5',6',7',8'-octahydro-1,1'-binaphthyl-2,2'-diyl phosphate], gadolinium tris[(R)-(−)-3,3'-diethenyl-1,1'-binaphthyl-2,2'-diyl phosphate], gadolinium tris[(S)-(+)-3,3'-diethenyl-1,1'-binaphthyl-2,2'-diyl phosphate], ytterbium tris[(R)-(−)-3,3'-diethenyl-1,1'-binaphthyl-2,2'-diyl phosphate], ytterbium tris[(S)-(+)-3,3'-diethenyl-1,1'-binaphthyl-2,2'-diyl phosphate], scandium tris[(R)-(−)-3,3'-diethenyl-1,1'-binaphthyl-2,2'-diyl phosphate] and scandium tris[(S)-(+)-3,3'-diethenyl-1,1'-binaphthyl-2,2'-diyl phosphate]. Further, such phosphates include one having from 0 to 10 molecules of water of crystallization when isolated as a crystal, and one in the form of a resin containing from 0 to 10 mol of water.

The catalyst of the present invention is a Lewis acid catalyst, and thus it can be applied to any conventional reaction using a Lewis acid, and it can induce asymmetry. Specific examples of such a reaction include asymmetric Diels-Alder cyclization reaction, asymmetric hetero Diels-Alder cyclization reaction, asymmetric reduction, asymmetric nitroaldol reaction, asymmetric protonation reaction, asymmetric Michael addition, asymmetric aldol condensation, asymmetric hydrophosphonyl reaction and asymmetric Michael-aldol reaction. However, the reaction is not particularly limited thereto.

The optical absolute configuration developed by the reaction using the catalyst for asymmetric synthesis of the present invention, usually depends on the optical absolute configuration of the binaphthol constituting the catalyst for asymmetric synthesis. Namely, in the case where the optical absolute configuration of the asymmetric carbon of the product is (R) configuration when a (R)-binaphthol is used, for example, the optical absolute configuration of the asymmetric carbon of the product is (S) configuration when a (S)-binaphthol as the enantiomer is used. Further, with respect to the optical absolute configuration of the asymmetric carbon of the product, the product does not always have (R) configuration in the case of using a (R)-binaphthol, but the optical absolute configuration of the product may change depending upon the type of the substrate, the type of the binaphthol and the type of the phosphate-forming element.

The catalyst of the present invention is prepared by converting the binaphthol monophosphoric acid derivative of the present invention to an alkali metal salt of e.g. lithium, sodium, potassium, rubidium or cesium, followed by reaction with a halide, sulfate, perchlorate, perbromate, tetrafluoroborate, trifluoromethanesulfonate or pentafluoroethanesulfonate of the salt-forming element.

The molar ratio of the binaphthol monophosphoric acid derivative to the salt-forming element is theoretically 1 to 3. However, for preparation, the binaphthol monophosphoric acid derivative is used in an amount of from 1.01 to 1.2 equivalent amount based on the salt-forming element, the binaphthol monophosphoric acid derivative is converted to its phosphate by an alkali metal hydroxide in an amount of from 0.9 to 1.05 times molar amount based on the binaphthol monophosphoric acid derivative, followed by reaction with the salt-forming element.

When the catalyst of the present invention is used for a reaction, a ligand may be added to the reaction system as the case requires, and specific examples of the ligand include amines such as diethylamine, triethylamine, n-propylamine, di-n-propylamine, tri-n-propylamine, tert-butylamine, di-tert-butylamine, cyclohexylamine, N,N-dimethylcyclohexylamine, piperidine, 1-methylpiperidine, 2,6-dimethylpiperidine, 1,2,6-trimethylpiperidine, 2,2,6,6-tetramethylpiperidinepyridine, piperazine, N,N'-dimethylpiperazine, aniline, N,N-dimethylaniline, 2-picoline, 2-ethylpiridine, 2,4-lutidine, 2,6-lutidine, 3,5-lutidine, 2,6-di-tert-butylpyridine, 2,6-bis(phenylethyl) pyridine, 2,4,6-collidine and chinaldine, phosphine oxides such as triphenylphosphine oxide, tri(2-methylphenyl) phosphine oxide, tri(3-methylphenyl)phosphine oxide, tri(4-methylphenyl)phosphine oxide, methyldiphenylphosphine oxide, methoxymethyl(diphenyl)phosphine oxide, tri-n-butylphosphine oxide, tri-n-octylphosphine oxide and tri (cyclohexyl)phosphine oxide, triamidephosphates such as hexamethyltriamidephosphate and tripiperidinophosphine oxide, and 1,3-dimethyl-2-imidazolidinone and 2,6-lutidine-N-oxide. The ligand may be added in an amount of from 0 to 5 molar amount based on the salt-forming element, as the case requires.

When the reaction is carried out by using the catalyst of the present invention, for removal of water in the system, a zeolite such as A type zeolite represented by molecular sieve 3A, 4A or 5A, molecular sieve 13X, Y type zeolite or L type zeolite may be used during the reaction as the case requires.

Now, an asymmetric hetero Diels-Alder cyclization reaction to which the catalyst of the present invention is applied, will be explained below as an example.

In the asymmetric hetero Diels-Alder cyclization reaction using the catalyst of the present invention, the catalyst may be used in any amount based on an aldehyde and a ketone or a diene to be subjected to the reaction. However, too excessive amount of its use is uneconomical, and if its amount is too small, the reaction may not proceed smoothly, or the catalyst may be deactivated due to a slight amount of impurities present in the system, whereby the reaction may not proceed at all in some cases. Accordingly, the amount of the catalyst is preferably within a range of from 0.01 mol % to 100 mol %, more preferably from 0.1 mol % to 50 mol %, based on the aldehyde and the ketone or the diene.

As the aldehyde applicable to the present invention, any aldehyde is applicable, and specific examples include ethyl formate, methoxycarbonylaldehyde, acetaldehyde, propionaldehyde, n-butanal, isobutanal, n-pentanal, acrolein, crotonaldehyde, cyclohexylaldehyde, benzaldehyde, 4-methoxybenzaldehyde, 4-methylbenzaldehyde, 3,5-dimethylbenzaldehyde, 4-phenylbenzaldehyde, 4-chlorobenzaldehyde, 4-nitrobenzaldehyde, naphthyl-2-aldehyde, 2-furfural, cinnamaldehyde, 3-phenylpropanal and 2-benzyloxyacetaldehyde, and as an aldehyde analogous compound, benzylimine or phenylthioamide may, for example, be mentioned.

The ketone applicable to the present invention may, for example, be acetophenone, (4-methylphenyl)acetophenone, (3-methylphenyl)acetophenone, (2-methylphenyl) acetophenone, (4-ethylphenyl)acetophenone, (3-ethylphenyl)acetophenone, (2-ethylphenyl) acetophenone, (4-i-propylphenyl)acetophenone, (3-i-propylphenyl)acetophenone, (2-i-propylphenyl) acetophenone, 1-phenylpropan-1-one, 1-(4-methylphenyl) propan-1-one, 1-(3-methylphenyl)propan-1-one, 1-(2-methylphenyl)propan-1-one, 1-phenyl-n-butan-1-one, 1-(4-methylphenyl)-n-butan-1-one, 1-(3-methylphenyl)-n-butan-1-one, 1-(2-methylphenyl)-n-butan-1-one, 1-phenyl-2-methylpropan-1-one, 1-(4-phenyl)-2-methylpropan-1-one, 1-(3-phenyl)-2-methylpropan-1-one, 1-(2-phenyl)-2-methylpropan-1-one, 1-phenyl-n-pentan-1-one, 1-phenyl-n-hexan-1-one, 1-phenyl-n-heptan-1-one, 1-phenyl-n-octan-1-one, 1-phenyl-n-nonan-1-one, 1-phenyl-n-decan-1-one, 1-phenyl-n-undecan-1-one, 1-phenyl-n-dodecan-1-one, 1-phenyl-n-tridecan-1-one, 1-phenyl-n-tetradecan-1-one, 1-phenyl-n-pentadecan-1-one, 1-phenyl-n-hexadecan-1-one, methyl-tert-butylketone, ethylglyoxylate, ethylphenylglyoxylate, methylphenylglyoxylate, ethyl i-propylglyoxylate, ethylphenylethenylglyoxylate or ethyl-cyclohexylglyoxylate.

The diene applicable to the present invention is not particularly limited, and specific examples of the diene include 1,3-butadiene, 1,3-pentadiene, cyclopentadiene, 1-methoxy-3-(trimethylsilyloxy)-1,3-butadiene (Danishefsky's diene), 1,3-bis(trimethylsilyloxy)-1,3-butadiene, 1-methoxy-3-(trimethylsilyloxy)-1,3-pentadiene, 1-methoxy-2-acetoxy-3-(trimethylsilyloxy)-1,3-butadiene, 1-methoxy-2-methyl-3-(trimethylsilyloxy)-1,3-butadiene, 1-tert-butoxy-3-(trimethylsilyloxy)-1,3-butadiene, 1-methoxy-3-(triethylsilyloxy)-1,3-butadiene, 1-tert-butoxy-3-(triethylsilyloxy)-1,3-butadiene, 2-methoxy-4-(trimethylsilyloxy)-1,3-pentadiene and 1-(trimethylsilyloxy)-1,3-methoxy-1,3-butadiene.

A heterocyclic compound of the following formula (9):

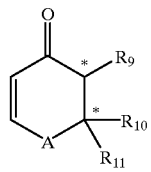

(9)

wherein symbol * represents an asymmetric carbon atom, each of $R_9$ and $R_{10}$ which are independent of each other, is a $C_{1-20}$linear or branched alkyl group, a $C_{2-20}$linear or branched alkenyl group, a $C_{2-20}$linear or branched alkynyl group, a phenyl group, a phenyl group having its nucleus substituted at the 1- to 4-carbon atom by a $C_{1-10}$ linear or branched alkyl group, a phenyl group having its nucleus substituted at the 1- to 4-carbon atom by a $C_{2-10}$ linear or branched alkenyl group, a phenyl group having its nucleus substituted at the 1- to 4-carbon atom by a $C_{2-10}$ linear or branched alkynyl group, a phenyl group having its nucleus substituted at the 1- to 4-carbon atom by a $C_{1-10}$ linear or branched alkoxy group, a naphthyl group, a $C_{3-8}$ cycloalkyl group, a $C_{1-10}$ alkyl group having a phenyl group, or a $C_{1-10}$ alkyl group having a phenyl group having its nucleus substituted at the 1- to 4-carbon atom by a $C_{1-10}$ linear or branched alkyl group, $R_9$ may be a hydrogen atom, $R_{11}$ is hydrogen, a $C_{1-20}$ linear or branched alkyl group, a $C_{2-20}$ linear or branched alkenyl group, a $C_{2-20}$linear or branched alkynyl group, a phenyl group, a phenyl group having its nucleus substituted at the 1- to 4-carbon atom by a $C_{1-10}$ linear or branched alkyl group, a phenyl group having its nucleus substituted at the 1- to 4-carbon atom by a $C_{2-10}$ linear or branched alkenyl group, a phenyl group having its nucleus substituted at the 1- to 4-carbon atom by a $C_{2-10}$ linear or branched alkynyl group, a phenyl group having its nucleus substituted at the 1- to 4-carbon atom by a $C_{1-10}$ linear or branched alkoxy group, a naphthyl group, a $C_{3-8}$ cycloalkyl group, a $C_{1-10}$ alkyl group having a phenyl group, a $C_{1-10}$ alkyl group having a phenyl group having its nucleus substituted at the 1- to 4-carbon atom by a $C_{1-10}$ linear or branched alkyl group, a $C_{1-19}$ linear or branched alkylcarbonyl group, a $C_{2-19}$ linear or branched alkenylcarbonyl group, a $C_{2-19}$ linear or branched alkynylcarbonyl group, a phenylcarbonyl group, a phenylcarbonyl group having its nucleus substituted at the 1- to 4-carbon atom by a $C_{2-19}$ linear or branched alkyl group, a phenylcarbonyl group having its nucleus substituted at the 1- to 4-carbon atom by a $C_{2-9}$ linear or branched alkenyl group, a phenylcarbonyl group having its nucleus substituted at the 1- to 4-carbon atom by a $C_{2-9}$ linear or branched alkynyl group, a naphthylcarbonyl group, a $C_{3-8}$ cycloalkylcarbonyl group, a $C_{1-9}$ alkylcarbonyl group having a phenyl group, a $C_{1-9}$ alkylcarbonyl group having a phenyl group having its nucleus substituted at the 1- to 4-carbon atom by a $C_{1-9}$ linear or branched alkyl group, a $C_{1-9}$ linear or branched alkyloxycarbonyl group, a phenyloxycarbonyl group, or a phenyloxycarbonyl group having its nucleus substituted at the 1- to 4-carbon atom by a $C_{1-19}$ linear or branched alkyl group, provided that $R_{10}$ and $R_{11}$ are not the same, and A is an oxygen, nitrogen, sulfur or selenium atom, obtainable by the method of the present invention, may be produced by any combination of the above aldehyde or ketone with diene, and the stereostructure of the carbons to which the substituents Rg, $R_{10}$ and $R_{11}$ are bonded, varies depending upon the type of the catalyst and the type of the reaction substrate.

In the reaction of the present invention, the aldehyde and the diene are reacted in an equimolar amount, and as the case requires, the aldehyde may be used in an amount of from 0.9 to 1.1 mol relative to the diene.

As a solvent applicable to the asymmetric hetero Diels-Alder cyclization reaction of the present invention, any solvent may be applicable so long as it is inert to the reaction. Specifically, a halogen solvent such as carbon tetrachloride, chloroform, dichloromethane, 1,2-dichloroethane, 1,1,1-trichloroethane, 1,1,2-trichloroethane, bromoform or dibromomethane may, for example, be mentioned.

The reaction temperature in the asymmetric hetero Diels-Alder cyclization reaction of the present invention varies depending upon the substrate to be subjected to the reaction. The reaction can be carried out usually within a range of from −78° C. to 100° C., and a high yield and a high optical purity can be obtained within a temperature range of from −20 to 50° C. in many reactions.

The concentration of the substrate in the asymmetric hetero Diels-Alder cyclization reaction of the present invention is not particularly limited, and it is usually within a range of from 0.1 wt % to 50 wt % based on the solvent.

The reaction time for the asymmetric hetero Diels-Alder cyclization reaction of the present invention varies depending upon the types of the substrate and the catalyst to be subjected to the reaction, and the reaction will be completed usually within 96 hours.

After the reaction has been completed, although the after-treatment operation is not defined, specific examples of which include a method of adding an appropriate amount of trifluoroacetic acid, adding pyridine and water followed by extraction with dichloromethane, and drying over magnesium sulfate followed by concentration to obtain crude desired compound. For purification of the desired compound, a conventional method such as silica gel preparative thin layer chromatography or preparative column chromatography, or distillation or recrystallization, may be employed.

Now, the present invention will be explained in further detail with reference to Examples. However, it should be understood that the present invention is by no means restricted to such specific Examples.

MEASUREMENT OF OPTICAL ROTATION

SEPA-300 manufactured by HORIBA was used.

MEASUREMENT OF MELTING POINT

MP-500D manufactured by YANAKO K.K. was used.

MEASUREMENT OF $^1$H-NMR AND $^{13}$C-NMR SPECTRUM

JNM-EX400 manufactured by JOEL was used (400 MHz).

MEASUREMENT OF HR FAB MASS SPECTRUM

JMS-HX110 manufactured by JOEL was used.

MEASUREMENT OF IR SPECTRUM

JIR-WINSPEC50 manufactured by JOEL was used.

MEASUREMENT OF ELEMENTAL ANALYSIS

Elemental analyses were accomplished at the service center for the elementary analysis of organic compounds, Kyushu University.

Test of Optical Purity

The optical purity was measured by a high performance liquid chromatography having a chiral column OD manufactured by Daicel K. K. fitted thereto (eluting solution: hexane/i-PrOH=2/1–100/1 (vol/vol), flow rate:1 ml/min).

REFERENCE EXAMPLE 1

Preparation of (R)-(−)-6,6'-di-n-octyl-1,1'-binaphthyl-2,2'-diol

To an egg-plant type flask of 500 ml having a magnet stirrer put therein, 10.0 g (16.02 mmol) of (R)-(−)-6,6'-dibromo-2,2'-dibenzyl ether, 590 mg (1.602 mmol) of bistriphenylphosphine dichloropalladium, 310 mg (1.602 mmol) of cuprous chloride, 590 mg (1.602 mmol) of tert-n-butylammonium iodide, 106 ml of triethylamine and 14 ml (96.12 mmol) of 1-octyne were charged, and they were heated with stirring to carry out the reaction at 80° C. for 12 hours.

After the reaction had been completed and the reaction mixture was cooled to room temperature, 300 ml of diethyl ether was added, and the reaction mixture was flowed through a column having Celite packed therein to remove a solid, followed by concentration and drying, to obtain 10.9 g of crude (R)-(−)-6,6'-(1-octenyl)-1,1'-binaphthyl-2,2'-dibenzyl ether.

The obtained (R)-(−)-6,6'-(1-octenyl)-1,1'-binaphthyl-2,2'-dibenzyl ether was directly used for the successive reaction without purification.

In an egg-plant type flask of 500 ml having a stirrer put therein, 10.6 g of the crude (R)-(−)-6,6'-(1-octenyl)-1,1'-binaphthyl-2,2'-dibenzyl ether, 150 ml of ethyl acetate and 2.78 ml of N,N-diisopropylethylamine were put, the atmosphere in the system was replaced by argon, then 1.09 g of 10% palladium on carbon was put therein, the atmosphere in the system was replaced by hydrogen, and the reaction was carried out with stirring at room temperature for 12 hours.

The obtained reaction solution was flowed through a column having Celite packed therein to remove the catalyst, followed by concentration, purification by silica gel column chromatography (hexane/ethyl acetate=19/1) and concentration, to obtain 4.26 g (yield: 52%/2 steps) of a transparent yellowish liquid.

Results of Analysis

Rf=0.46(hexane/ethyl acetate=4/1) Optical rotation:$[\alpha]_D^{24}$−58.00° (c=1.2CHCl$_3$) $^1$H-NMR (CDCl$_3$) δ 7.90(d, 2H, J=9.27 Hz, C$_{20}$H$_{10}$), 7.66(s, 2H, C$_{20}$H$_{10}$), 7.35(d, 2H, J=9.27 Hz, C$_{20}$H$_{10}$), 7.16(d, 2H, J=8.79 Hz, C$_{20}$H$_{10}$), 7.08(d, 2H, J=8.30 Hz, C$_{20}$H$_{10}$), 4.97 (br, 2H, OH), 2.71(t, 4H, J=7.82 Hz, CH$_2$CH$_2$(CH$_2$)$_5$CH$_3$), 1.68–1.64(m, 4H, CH$_2$CH$_2$(CH$_2$)$_5$CH$_3$), 1.32–1.24(m, 20H, CH$_2$CH$_2$(CH$_2$)$_5$CH$_3$), 0.87(t, 6H, J=6.84 Hz, CH$_2$CH$_2$(CH$_2$)$_5$CH$_3$) $^{13}$C-NMR(CDCl$_3$) δ 152.05, 138.63, 131.68, 130.79, 129.60, 128.99, 126.85, 124.13, 117.60, 110.85, 35.78, 31.88, 31.43, 29.49, 29.38, 29.25, 22.67, 14.11. HR FAB mass spectrum m/z measured value 510.3477(M)$^+$, (calculated value C$_{36}$H$_{46}$O$_2$:510.3498). Elemental analysis(%)

measured value C, 84.62; H9.08

(calculated value C$_{36}$H$_{46}$O$_2$:C, 84.66; H9.08.

REFERENCE EXAMPLE 2

Preparation of (R)-(−)-6,6'-bis(2",6"-dimethylphenyl)-1,1'-binaphthyl-2,2'-diol

To an egg-plant type three neck distillation flask of 100 ml equipped with a magnet stirrer, a septum cap and a reflux condenser, 889 mg (0.7693 mmol) of tetrakis (triphenylphosphine)palladium, 3.00 g (20.00 mmol) of 2,6-xylylboronic acid and 7.28 g (23.08 mmol) of barium hydroxide.8H$_2$O were charged. Then, the atmosphere in the system was replaced by argon, a solution having 4.80 g (7.693 mmol) of 2,2'-dibenzyloxy-6,6'-dibromo-1,1'-binaphthyl dissolved in 46.2 ml of 1,2-dimethoxyethane was injected into the system through the septum by a syringe of 50 ml, and 7.7 ml of water was further added.

The obtained mixture was heated to 80° C. with stirring on an oil bath, and the reaction was carried out at the same temperature for 2.5 hours.

After the reaction had been completed, the reaction mixture was cooled to room temperature, and extraction with toluene, washing with saturated aqueous sodium chloride, drying over magnesium sulfate, concentration and purification by silica gel column chromatography (hexane/ethyl acetate=8/2–7/3) were carried out to obtain 5.3 g (yield: 97%) of (R)-(+)-2,2'-dibenzyloxy-1,1'-binaphthyl-6,6'-di (2",6"-dimethylphenyl) H$_2$O as a colorless crystal.

Results of Analysis

Melting point 89.6° C. Rf=0.44(hexane/ethyl acetate=9/1); Optical rotation:$[\alpha]_D^{20}$+89.0° (c=1.0CHCl$_3$); $^1$H-NMR (CDCl$_3$) δ 7.92(d, 2H, J=8.79 Hz, aromatic), 7.91(s, 2H, aromatic), 7.45(dd, 4H, J=8.79, 8.30 Hz, aromatic), 7.20–7.07(m, 14H, aromatic), 6.96(d, 4H, J=6.83 Hz, aromatic), 5.08(s, 4H, OCH$_2$), 2.08(d, 12H, J=4.39 Hz, CH$_3$); $^{13}$C-NMR(CDCl$_3$) δ 153.85, 141.78, 137.41, 136.35, 132.94, 129.54, 129.27, 128.99, 128.19, 128.06, 127.55, 127.29, 127.24, 126.98, 126.78, 125.77, 120.69, 115.94, 71.02, 21.04, 21.00 IR(KBR, (ν cm$^{-1}$)3712, 3061, 3030, 2947, 2918, 1589, 1483, 1452 HR FAB mass spectrum m/z measured value 674.3142(M)$^+$, (calculated value C$_{50}$H$_{42}$O$_2$:674.3185) Elemental analysis(%)

measured value C, 86.60; H, 6.15

(calculated value C$_{50}$H$_{42}$O$_2$.H$_2$O:C, 86.67; H, 6.40).

To an egg-plant type flask of 100 ml having a magnet stirrer put therein, 1.49 g (2.102 mmol) of the (R)-(+)-2,2'-dibenzyloxy-1,1'-binaphthyl-6,6'-di( 2",6"-dimethylphenyl) .H$_2$O, 385 μl (2.208 mmol) of N,N-diisopropylethylamine and 22 ml of ethyl acetate were charged, the atmosphere in the system was replaced by argon, and 149 g of 10% palladium on carbon was charged thereto. Then, the atmosphere in the system was replaced by hydrogen, and the reaction was carried out with stirring at room temperature for 12 hours.

After the reaction had been completed, a solid was removed by a column having Celite packed therein, followed by concentration and purification by silica gel column chromatography (hexane/ethyl acetate=19/1–4/1) to obtain 1.07 g (yield: 97%) of the desired compound (R)-(−)-6,6'-bis(2",6"-dimethylphenyl)-1,1'-binaphthyl-2,2'-diol-H$_2$O as a pale yellow solid.

Results of Analysis

Rf=0.31(hexane/ethyl acetate=4/1) Optical rotation:$[\alpha]_D^{27}$−62.90° (c=1.0, CHCl$_3$) $^1$H-NMR (CDCl$_3$) δ 7.97(d, 2H, J=8.79 Hz, C$_{20}$H$_{10}$), 7.68(s, 2H, C$_{20}$H$_{10}$), 7.42(d, 2H, J=8.79 Hz, C$_2$OH$_{10}$), 7.33(d, 2H, J=8.79 Hz, C$_{20}$H$_{10}$), 7.21–7.14(m, 8H, C$_{20}$H$_{10}$, C$_6$H$_3$(CH$_3$)$_2$), 2.07(s, 12H, CH$_3$) $^{13}$C-NMR(CDCl$_3$) δ 152.69, 141.34, 136.82, 136.31, 132.10, 131.35, 129.56, 129.30, 128.23, 127.35, 127.16, 124.29, 117.87, 110.92, 21.06 HR FAB mass spectrum m/z measured value 494.2240(M)$^+$, (calculated value C$_{36}$H$_{30}$O$_2$:494.2246) Elemental analysis (%)

measured value C, 84.05; H, 6.19

(calculated value $C_{36}H_{30}O_2 \cdot H_2O$:C, 84.35; H, 6.29).

EXAMPLE 1

Preparation of (R)-(−)-6,6'-di-n-octyl-1,1'-binaphthyl-2,2'-diyl phosphoric acid.1/4 $H_2O$ To an egg-plant type flask of 100 ml having a magnet stirrer put therein, 5.91 g (11.57 mmol) of (R)-(−)-6,6'-di-n-octyl-1,1'-binaphthyl-2,2'-diol and 12 ml of dichloromethane were charged followed by dissolution. Then, 2.32 ml (17.36 mmol) of phosphorus oxychloride was put therein, the reactor was subjected to an ice bath and cooled to 0° C., and 7.33 ml of a solution comprising 4.84 ml (34.71 mmol) of triethylamine and 3.05 ml of dichloromethane was dropwise added thereto over a period of 30 minutes. After the dropwise addition had been completed, stirring was carried out at the same temperature for 40 minutes, the temperature was recovered to room temperature, followed by stirring further for 1 hour to carry out the reaction.

After the reaction had been completed, the reaction mixture was cooled to 0° C., and addition of water, extraction with dichloromethane, drying over magnesium sulfate and concentration were carried out to obtain 6.69 g of crude (R)-(−)-6,6'-di-n-octyl-1,1'-binaphthyl-2,2'-diyl phosphate chloride. The obtained (R)-(−)-6,6 '-di-n-octyl-1,1'-binaphthyl-2,2'-diyl phosphoric chloride was directly used for the successive reaction without purification.

Results of Analysis

Rf 0.47(hexane/ethyl acetate=8/1) Optical rotation:$[\alpha]_D^{17}$−373.40° (c=1.0, $CHCl_3$) $^1$H-NMR ($CDCl_3$) δ 7. 99(dd, 2H, J=7.32, 7.82 Hz, $C_{20}H_{10}$), 7.74(d, 2H, J=6.34 Hz, $C_{20}H_{10}$), 7.57(d, 1H, J=8.79 Hz, $C_{20}H_{10}$), 7.49(d, 1H, J=8.79 Hz, $C_{20}H_{10}$), 7.33 (dd, 2H, J=9.28, 10.74 Hz, $C_{20}H_{10}$), 7.21–7.17(m, 2H, $C_{20}H_{10}$), 2.76(t, 4H, J=6.34 Hz, $CH_2CH_2(CH_2)_5CH_3$), 1.71–1.67(m, 4H, $CH_2CH_2(CH_2)_5CH_3$), 1.34–1.27(m, 20H, $CH_2CH_2(CH_2)_5CH_3$), 0.87(t, 6H, J=6.35 Hz, $CH_2CH_2(CH_2)_5CH_3$) $^{13}$C-NMR($CDCl_3$) δ 145.98, 145.85, 145.75, 145.64, 141.08, 132.38, 132.21, 131.17, 130.95, 130.49, 128.68, 127.11, 126.89, 126.84, 121.59, 121.44, 120.11, 119.76, 35.76, 31.85, 31.13, 31.08, 29.43, 29.36, 29.23, 22.65,14.09 HR FAB mass spectrum m/z measured value 591.2788(M+H)$^+$, (calculated value $C_{36}H45ClO_3P$:591. 2795) Elemental analysis(%)

measured value C, 73.27; H, 7.52

(calculated value $C_{36}H_{44}ClO_3P$:C, 73.14; H, 7.50)

To an egg-type flask of 200 ml equipped with a magnet stirrer and a reflux condenser, 1.68 g (2.842 mmol) of the obtained crude (R)-(−)-6,6'-di-n-octyl-1,1'-binaphthyl-2,2'-diyl phosphoric chloride, 50 ml of a 2% sodium carbonate aqueous solution and 10 ml of tetrahydrofuran (hereinafter referred to simply as THF) were charged, and the mixture was heated to from 75 to 85° C. with stirring on an oil bath to carry out the reaction for 5 hours.

After the reaction had been completed, the reaction mixture was cooled to room temperature and further held in a refrigerator for 12 hours, and the precipitate was collected by filtration and washed with a 2% sodium carbonate aqueous solution.

To an egg-plant type flask of 100 ml equipped with a stirrer and a reflux condenser, the obtained precipitate, 23.1 ml of water, 1.8 ml of 35% hydrochloric acid and 10 ml of THF were charged, and the mixture was heated to 80° C. with stirring on an oil bath to carry out the reaction for 4 hours. After the reaction had been completed, the reaction mixture was cooled to room temperature, and extraction with dichloromethane, washing with water, drying over magnesium sulfate, concentration and drying under reduced pressure at 110° C. for 12 hours, were carried out, to obtain 1.46 g (yield: 90%) of the desired compound (R)-(−)-6,6'-di-n-octyl-1,1'-binaphthyl-2,2'-diyl phosphoric acid as a blackish brown viscous substance.

Results of Analysis

Optical rotation:$[\alpha]_D^{21}$−296.30° (c=1.0 , $CHCl_3$) $^1$H-NMRR($CDCl_3$) δ 7.89(d, 2H, J=8.79 Hz, $C_{20}H_{10}$), 7.69 (s, 2H, $C_{20}H_{10}$), 7.50(d, 2H, J=8.79 Hz, $C_{20}H_{10}$), 7.33(d, 2H, J=8.30 Hz, $C_{20}H_{10}$), 7.16(d, 2H, J=8.79 Hz, $C_{20}H_{10}$), 2.75(t, 4H, J=7.32 Hz, $CH_2CH_2(CH_2)_5CH_3$), 1.69–1.67(m, 4H, $CH_2CH_2(CH_2)_5CH_3$), 1.33–1.27(m, 20H, $CH_2CH_2(CH_2)_5CH_3$), 0.88 (dd, 6H, J=7.33, 6.34 Hz, $CH_2CH_2(CH_2)_5CH_3$) $^{13}$C-NMR($CDCl_3$) δ 146.20, 140.40, 136.09, 132.05, 130.64, 128.28, 127.04, 126.76, 121.31, 120.38, 35.78, 31.87, 31.17, 29.47, 29.36, 29.25, 22.67, 20 14.11 IR(KBr, ν cm$^{-1}$)3853, 3735, 3649, 3307, 2926, 2854 HR FAB mass spectrum m/z measured value 573.3134(M+H)$^+$, (calculated value $C_{36}H_{46}O_4P$:573. 3134) Elemental analysis(%)

measured value C, 74.94; H, 8.06

(calculated value $C_{36}H_{45}O_4P$-1/4$H_2O$:C, 74.91; H, 7.95)

EXAMPLE 2

Preparation of (R)-(−)-6,6'-bis(2,6-dimethylphenyl)-1,1'-binaphthyl-2,2'-diyl phosphoric acid.1/2 $H_2O$ The same operation as in Example 1 was carried out except that (R)-(−)-6,6'-di-n-octyl-1,1'-binaphthyl-2,2'-diol (5.91 g, 11.57 mmol) used in Example 1 was changed into 5.73 g (11.57 mmol) of (R)-(−)-6,6'-bis(2,6-dimethylphenyl)-1,1'-binaphthyl-2,2'-diol, to obtain 6.92 g (yield: quant.) of (R)-(−)-6,6'-bis(2,6-dimethylphenyl)-1,1'-binaphthyl-2,2'-diyl phosphoric chloride as a white solid.

Results of Analysis

Rf 0.55(hexane/ethyl acetate=4/1) Optical rotation:$[\alpha]_D^{21}$−301.900° (c=1.0, $CHCl_3$) $^1$H-NMR($CDCl_3$) δ 8.08(q, 2H, J=4.40 Hz, $C_{20}H_{10}$), 7.79(d, 2H, J=5.86 Hz, $C_{20}H_{10}$), 7.67(d, 1H, J=8.78 Hz, $C_{20}H_{10}$), 7.58(d, 2H, J=8.78 Hz, $C_{20}H_{10}$), 7.55(d, 1H, J=8.79 Hz, $C_{20}H_{10}$), 7.22–7.12(m, 8H, $C_{20}H_{10}$, $C_6H_3(CH_3)_2$), 2.13(s, 6H, $CH_3$), 2.00(s, 6H, $CH_3$) $^{13}$C-NMR($CDCl_3$) δ 146.17, 140.62, 139.23, 136.09, 135.96, 135.85, 132.38, 132.19, 131.85, 131.61, 130.93, 128.96, 128.33, 127.44, 127.37, 127.27, 127.15, 126.32, 121.57, 120.42, 119.98, 20.95, 20.89, 20.82 IR(KBr, ν cm$^{-1}$)3733, 3338, 3020, 2975, 1475, 1461, 1317, 960, 678 HR FAB mass spectrum m/z measured value 574.1460(M)$^+$, (calculated value $C_{36}H_{28}ClO_3P$:574.1465)

To an egg-type flask of 200 ml equipped with a magnet stirrer and a reflux condenser, 1.57 g (2.730 mmol) of the obtained (R)-(−)-6,6'-bis(2,6-dimethylphenyl)-1,1'-binaphthyl-2,2'-diyl phosphoric chloride and 48 ml of a 2% sodium carbonate aqueous solution were charged, and the mixture was heated to from 80 to 110° C. with stirring on an oil bath to carry out the reaction for 1 hour.

After the reaction had been completed, the reaction mixture was cooled to room temperature and further held in a refrigerator for 12 hours, and the precipitate was collected by filtration and washed with a 2% sodium carbonate aqueous solution.

To an egg-plant type flask of 100 ml equipped with a stirrer and a reflux condenser, the obtained precipitate, 22.2 ml of water and 1.7 ml of 35% hydrochloric acid were charged, and the mixture was heated to 95° C. with stirring on an oil bath to carry out the reaction for 1 hour.

After the reaction had been completed, the reaction mixture was cooled to room temperature, and extraction with dichloromethane, washing with water, drying over magnesium sulfate, concentration and drying under reduced pressure at 120° C. for 16 hours, were carried out to obtain 495 mg (yield: 33%) of the desired compound (R)-(–)-6,6'-bis(2,6-dimethylphenyl)-1,1'-binaphthyl-2,2'-diyl phosphoric acid as a colorless crystal.

Results of Analysis

Optical rotation:$[\alpha]_D^{26}$ –265.95° (c=1.0, CHCl$_3$) $^1$H-NMR(CDCl$_3$) δ 8.03(d, 2H, J=8.79 Hz, C$_{20}$H$_{10}$), 7.76(s, 2H, C$_{20}$H$_{10}$), 7.64(d, 2H, J=8.79 Hz, C$_{20}$H$_{10}$), 7.58(d, 2H, J=8.79 Hz, C$_{20}$H$_{10}$), 7.22–7.12(m, 8H, C$_{20}$H$_{10}$, C$_6$H$_3$(CH$_3$)$_2$), 2.14(s, 6H, CH$_3$), 1.99(s, 6H, CH$_3$) $^{13}$C-NMR (CDCl$_3$) δ 147.28, 147.19, 140.94, 138.32, 136.07, 135.96, 131.85, 131.10, 131.02, 128.32, 128.10, 127.38, 127.31, 127.24, 121, 61, 120.91, 20.91, 20.80 IR(KBr, ν cm$^{-1}$)3853, 3648, 3307, 1226, 1207, 1027, 950, 892, 767 HR FAB mass spectrum m/z measured value 557. 1879(M)$^+$, (calculated value C$_{36}$H$_{29}$O$_4$P:557. 1882) Elemental analysis(%)

measured value C, 76.54; H, 5.29

(calculated value C$_{36}$H$_{29}$O$_4$P.1/2H$_2$O:C, 76. 45; H, 5.35)

EXAMPLE 3

Preparation of (R)-(–)-5,6,7,8,5',6',7',8'-octahydro-1,1'-binaphthyl-2,2'-diyl phosphoric acid.1/4 H$_2$O To an egg-plant type flask of 100 ml having a magnet stirrer put therein, 1.14 g (3.87 mmol) of (R)-(–)-5,6,7,8,5',6',7',8'-octahydro-1,1'-binaphthyl-2,2'-diol, 710 μl (7.62 mmol) of phosphorus oxychloride and 8 ml of dichloromethane were charged in an argon atmosphere and stirred for dissolution, and 1.60 ml (11.5 mmol) of triethylamine was added thereto, to carry out the reaction at room temperature for 12 hours.

After the reaction had been completed, addition of water, extraction with 16 ml of dichloromethane, washing with water, drying over magnesium sulfate and concentration were carried out to obtain (R)-5,6,7,8,5',6',7',8'-octahydro-1,1'-binaphthyl-2,2'-diyl phosphoric chloride as a colorless solid.

Results of Analysis $^1$H-NMR(CDCl$_3$) δ 7.19–7.17(3H, Aromatic), 7.06(dd, 1H, J=1.95, 8.30 Hz), 2.90–2.78(m, 4H), 2.72–2. 63(m, 2H), 2.28 (dt, 2H, J=5. 37, 16.11 Hz), 1.86–1.77 (m, 6H), 1.63–1.51(m, 2H)

To an egg-plant type flask of 200 ml equipped with a magnet stirrer and a reflux condenser, the obtained (R)-5,6,7,8,5',6',7',8'-octahydro-1,1'-binaphthyl-2,2'-diyl phosphoric chloride, 85 ml of a 2% sodium carbonate aqueous solution and 10 ml of THF were charged, and the mixture was heated with stirring to carry out the reaction at 65° C. for 4 hours. After the reaction had been completed, the reaction mixture was cooled to room temperature, most of the THF was distilled off under reduced pressure, and the reaction mixture was held in a refrigerator for 12 hours. The solid precipitated by cooling was collected by filtration, washed with a 2% sodium carbonate aqueous solution and dried at 70° C. under reduced pressure, to obtain 1.42 g (yield: 97%) of sodium (R)-5,6,7,8,5',6',7',8'-octahydro-1,1'-binaphthyl-2,2'-diyl phosphate.

To an egg-plant type flask of 100 ml equipped with a stirrer and a reflux condenser, 1.01 g (2.67 mmol) of the sodium (R)-5,6,7,8,5',6',7',8'-octahydro-1,1'-binaphthyl-2,2'-diyl phosphate, 6 ml of 35% hydrochloric acid and 45 ml of water were charge and heated with stirring to carry out the reaction at 70° C. for 2 hours. After the reaction had been completed, the reaction mixture was cooled to room temperature, and the precipitate was collected by filtration, washed with water and dried at 120° C. for 10 hours, to obtain 982 mg (yield: 94%/2 steps) of (R)-5,6,7,8,5',6',7',8'-octahydro-1,1'-binaphthyl-2,2'-diyl phosphoric acid as a colorless solid.

Results of Analysis

Decomposition temperature 289° C. Optical rotation:$[\alpha]_D^{20}$ –250° (c=1.0, EtOH) $^1$H-NMR(CD$_3$OD) δ 7.22(d, 2H, J=8.30 Hz, Aromatic), 7.08(d, 2H, J=8.30 Hz, Aromatic), 2.91–2.86(m,4H), 2.80–2.72(m,2H), 2.30–2.23(m, 2H), 1.89–1.80(m, 6H), 1.61–1.55(m, 2H) $^{13}$C-NMR(CD$_3$OD) 5 147.98,147.88,139.45, 136.86, 131.11, 127.47, 119.34, 30.02, 28.87, 23.60, 23.47 IR(KBr, ν cm$^{-1}$)2935, 2858, 1471, 1439, 1423, 1311, 1263, 1252, 1227, 1157, 1056, 1049, 962, 904, 895, 833,816,710 HR FAB mass spectrum m/z measured value 357.1255(M+H)$^+$, (calculated value C$_{20}$H$_{22}$O$_4$P:357.1256) Elemental analysis(%)

measured value C, 66.48; H, 5.92

(calculated value C$_{20}$H$_{21}$O$_4$P.1/4H$_2$O:C, 66.57; H, 6.01)

EXAMPLE 4

Preparation of gadolinium tris[(R)-(–)-6,6'-di-n-octyl-1,1'-binaphthyl-2,2'-diyl phosphate].2H$_2$O To an egg-plant type flask of 50 ml equipped with a magnet stirrer and a reflux condenser, 203 mg (0.3544 mmol) of the (R)-(–)-6,6'-di-n-octyl-1,1'-binaphthyl-2,2'-diyl phosphoric acid obtained in Example 1, 115 μl (0.3443 mmol) of a 3N sodium hydroxide aqueous solution and 2.1 ml of methanol were charged and heated with stirring under reflux, a solution having 41.8 mg (0.1125 mmol as GdCl$_3$) of gadolinium chloride.6H$_2$O dissolved in 0.5 ml of methanol was gradually added thereto, and the reaction was carried out further for 12 hours under the same condition. After the reaction had been completed, the reaction mixture was cooled to room temperature, and the precipitate was collected by filtration, washed with methanol and dried at 125° C. under reduced pressure for 14 hours to obtain 196 mg (yield: 93%) of the desired compound gadolinium tris [(R)-(–)-6,6'-di-n-octyl-1,1'-binaphthyl-2,2'-diyl phosphate].2H$_2$O as a pale yellowish brown solid.

Results of Analysis

Optical rotation:$[\alpha]_D^{22}$ –195.50° (c=1.0, CHCl$_3$) IR(KBr, ν cm$^{-1}$)3853, 3735, 3649, 3307, 2926, 2852 Elemental analysis(%)

measured value C, 67.72; H, 7.23

(calculated value C$_{108}$H$_{132}$O$_{12}$P$_3$Gd.2H$_2$O:C, 67.97; H, 7.18)

EXAMPLE 5

Ytterbium tris[(R)-(−)-6,6'-di-n-octyl-1,1'-binaphthyl-2,2'-diyl phosphate].5H$_2$O The same operation as in Example 4 was carried out except that gadolinium chloride.6H$_2$O was changed into ytterbium chloride.6H$_2$O, to obtain the desired compound.

Results of Analysis

Optical rotation:[α]$_D^{22}$−155.15° (c=1.0, CHCl$_3$) IR(KBr, ν cm$^{-1}$)3853, 3735, 3649, 3307, 2924, 2852 Elemental analysis(%)

measured value C, 65.30; H, 7.17

(calculated value C$_{108}$H$_{132}$O$_{12}$P$_3$Yb.5H$_2$O:C, 65.57; H, 7.24)

EXAMPLE 6

Scandium tris[(R)-(−)-6,6'-di-n-octyl-1,1'-binaphthyl-2,2'-diyl phosphate].H$_2$O The same operation as in Example 4 was carried out except that gadolinium chloride.6H$_2$O was changed into scandium trichloride.6H$_2$O, to obtain the desired compound.

Results of Analysis

Optical rotation:[α]$_D^{23}$−346.90° (c=1.0, CHCl$_3$) IR(KBr, ν cm$^{-1}$)3853, 3735, 3649, 3307, 2924, 2852 Elemental analysis(%)

measured value C, 73.24; H, 7.75

(calculated value C$_{108}$H$_{132}$O$_{12}$P$_3$Sc.1H$_2$O:C, 72.95; H, 7.60)

EXAMPLE 7

Gadolinium tris[(R)-(−)-6,6'-di(2",6"-dimethylphenyl)-1,1'-binaphthyl-2,2'-diyl phosphate].4H$_2$O The same operation as in Example 4 was carried out except that (R)-(−)-6,6'-di-n-octyl-1,1'-binaphthyl-2,2'-diyl phosphoric acid was changed into the (R)-(−)-6,6'-bis(2,6-dimethylphenyl)-1,1'-binaphthyl-2,2'-diyl phosphoric acid.1/2H$_2$O, to obtain the desired compound.

Results of Analysis

Optical rotation:[α]$_D^{23}$−144.200 (c=1.0, CHCl$_3$) IR (KBr, ν cm$^{-1}$)3853, 3649, 3307, 1240, 1103 Elemental analysis (%)

measured value C, 68.24; H, 5.23

(calculated value C$_{108}$H$_{84}$O$_{12}$P$_3$Gd.4H$_2$O:C, 68.41; H, 4.89)

EXAMPLE 8

Ytterbium tris[(R)-(−)-6,6'-di(2",6"-dimethylphenyl)-1,1'-binaphthyl-2,2'-diyl phosphate].4H$_2$O, 5H$_2$O The same operation as in Example 4 was carried out except that (R)-(−)-6,6'-di-n-octyl-1,1'-binaphthyl-2,2'-diyl phosphoric acid was changed into the (R)-(−)-6,6'-bis(2,6-dimethylphenyl)-1,1'-binaphthyl-2,2'-diyl phosphoric acid.1/2H$_2$O obtained in Example 2, and gadolinium chloride.6H$_2$O was changed into ytterbium chloride.6H$_2$O, to obtain the desired compounds. According to the difference in the drying temperature, a tetrahydrate or a pentahydrate was formed.

Results of Analysis

Optical rotation:[α]$_D^{23}$−147.70° (c=1.0, CHCl$_3$) IR(KBr, ν cm$^{-1}$)3853, 3649, 3307, 1240, 1103 Elemental analysis (%) Tetrahydrate measured value C, 67.66; H, 4.91

(calculated value C$_{108}$H$_{84}$O$_{12}$P$_3$Yb.4H$_2$O:C, 67.85; H, 4.85) Pentahydrate measured value C, 67.08; H,4.71

(calculated value C$_{108}$H$_{84}$O$_{12}$P$_3$Yb.5H$_2$O:C, 67.22; H, 4.91)

EXAMPLE 9

Scandium tris[(R)-(−)-6,6'-di(2",6"-dimethylphenyl)-1,1'-binaphthyl-2,2'-diyl phosphate].4H$_2$O The same operation as in Example 4 was carried out except that (R)-(−)-6,6'-di-n-octyl-1,1'-binaphthyl-2,2'-diyl phosphoric acid was changed into the (R)-(−)-6,6'-bis(2,6-dimethylphenyl)-1,1'-binaphthyl-2,2'-diyl phosphoric acid.1/2H$_2$O obtained in Example 2, and gadolinium chloride.6H$_2$O was changed into scandinium trichloride.6H$_2$O, to obtain the desired compound.

Results of Analysis

Optical rotation:[α]$_D^{23}$−107.40° (c=1.0, CHCl$_3$) HR FAB mass spectrum m/z 1711.4819 (M+H)$^+$ (calculated value C$_{108}$H$_{85}$O$_{12}$P$_3$Sc:C, 1711.4813) Elemental analysis(%)

measured value C, 72.62; H, 5.64

(calculated value Cg$_{108}$H$_{84}$O$_{12}$P$_3$Sc.4H$_2$O:C, 72.72; H, 5.20)

EXAMPLE 10

Scandium tris[(R)-(−)-5,6,7,8,5',6',7',8'-1,1'-binaphthyl-2,2'-diyl phosphate].4H$_2$O The same operation as in Example 4 was carried out except that (R)-(−)-6,6'-di-n-octyl-1,1'-binaphtyl-2,2'-diyl phosphoric acid was changed into the (R)-(−)-5,6,7,8,5',6',7',8'-octahydro-1,1'-binaphthyl-2,2'-diyl phosphoric acid.1/4H$_2$O obtained in Example 3, and gadolinium chloride.6H$_2$O was changed into scandinium trichloride.6H$_2$O, to obtain the desired compound.

Results of Analysis

Appearance colorless solid Decomposition temperature 248° C. IR(KBr, ν cm$^{-1}$)2931, 2858, 1471, 1448, 1437, 1423,1252,1225,1111,1057,962,889,877,833,812 Elemental analysis(%)

measured value C, 61.05; H, 5.45

(calculated value C$_{60}$H$_{60}$O$_{12}$P$_3$Sc.4H$_2$O:C, 60.91; H, 5.79)

EXAMPLE 11

Synthesis of 2-phenyl-2,3-dihydro-4H-pyran-4-one

To a round flask of 5 ml having a magnet stirrer put therein, 19.1 mg (0.01 mmol) of the catalyst (tetrahydrate) obtained in Example 8 and 1 ml of dichloromethane were added for dissolution, then benzaldehyde (10 μl, 0.1 mmol) and 1-methoxy-3-trimethylsilyloxy-1,3-butadiene (purity: 90%, 30.0 μl, 0.150 mmol) were added thereto, and the reaction was carried out at room temperature for 24 hours. After the reaction had been completed, two drops of trifluoroacetic acid was added by a microsyringe, three drops of pyridine was added by a microsyringe, and 1 ml of water was added. Successively, extraction with dichloromethane, drying over anhydrous magnesium sulfate, concentration and purification by preparative silica gel column chromatography (hexane/ethyl acetate=4/1) were carried out to obtain 16.1 mg of the desired compound (R)-2-phenyl-2,3-dihydro-4H-pyran-4-one. As a result of analysis, the yield was 93% and the optical purity was 19% (R).

EXAMPLES 12 TO 18

The reaction was carried out under conditions as shown in Table 1 using the same reaction apparatus as in Example 11. The results are shown in Table 1. Conditions which are not shown in Table 1 were the same as in Example 11.

TABLE 1

| | Catalyst | Reaction time (hrs) | Yield (%) | Optical purity (ee%) | Configuration (R/S) |
|---|---|---|---|---|---|
| EXAMPLE 12 | 1 | 24 | 63 | 34 | (R) |
| EXAMPLE 13 | 2 | 24 | 59 | 34 | (R) |
| EXAMPLE 14 | 3 | 24 | 83 | 52 | (R) |
| EXAMPLE 15 | 4 | 24 | 77 | 26 | (S) |
| EXAMPLE 16 | 5 | 24 | 91 | 59 | (S) |
| EXAMPLE 17 | 6 | 24 | 82 | 23 | (S) |
| EXAMPLE 18 | 7 | 16 | 95 | 96 | (R) |

Catalyst 1: The compound obtained in Example 4; gadolinium tris[(R)-(−)-6,6'-dioctyl-1,1'-binaphthyl-2,2'-diyl phosphate].2H$_2$O Catalyst 2: The compound obtained in Example 5; ytterbium tris[(R)-(−)-6,6'-dioctyl-1,1'-binaphthyl-2,2'-diyl phosphate].5H$_2$O Catalyst 3: The compound obtained in Example 6; scandium tris[(R)-(−)-6,6'-dioctyl-1,1'-binaphthyl-2,2'-diyl phosphate]·H$_2$O Catalyst 4: The compound obtained in Example 7; gadolinium tris[(R)-(−)-6,6'-di(2",6"-dimethylphenyl)-1,1'-binaphthyl-2,2'-diyl phosphate].4H$_2$O Catalyst 5: The compound obtained in Example 8; ytterbium tris[(R)-(−)-6,6'-di(2",6"-dimethylphenyl)-1,1'-binaphthyl-2,2'-diyl phosphate].5H$_2$O Catalyst 6: The compound obtained in Example 9; scandium tris[(R)-(−)-6,6'-di(2",6"-dimethylphenyl)-1,1'-binaphthyl-2,2'-diyl phosphate].4H$_2$O Catalyst 7: The compound obtained in Example 10; scandium tris[(R)-(−)-5,6,7,8,5',6',7',8'-1,1'-binaphthyl-2,2'-diyl phosphate]

EXAMPLE 19

Synthesis of 2-(4-methoxyphenyl)-2,3-dihydro-4H-pyran-4-one

The same operation as in Example 11 was carried out except that the compound obtained in Example 10: scandium tris[(R)-(−)-5,6,7,8,5',6',7',8'-1,1'-binaphthyl-2,2'-diyl phosphate] was used as a catalyst, benzaldehyde was changed into 4-methoxybenzaldehyde, and the reaction was carried out at room temperature for 16 hours, to obtain 2-(4-methoxyphenyl)-2,3-dihydro-4H-pyran-4-one with a yield of 99% with an optical purity of 94% ee(R).

EXAMPLE 20

Synthesis of 2-isopropyl-2-ethoxycarbonyl-2,3-dihydro-4H-pyran-4-one

The same operation as in Example 11 was carried out except that the compound obtained in Example 10: scandium tris[(R)-(−)-5,6,7,8,5',6',7',8'-1,1'-binaphthyl-2,2'-diyl phosphate] was used as a catalyst, benzaldehyde was changed into ethylisopropylglyoxylate, and the reaction was carried out at room temperature for 16 hours, to obtain 2-isopropyl-2-ethoxycarbonyl-2,3-dihydro-4H-pyran-4-one with a yield of 10% with an optical purity of 45% ee(R).

EXAMPLE 21

Synthesis of 2-methyl-2-ethoxycarbonyl-2,3-dihydro-4H-pyran-4-one

The same operation as in Example 11 was carried out except that the compound obtained in Example 10: scandium tris[(R)-(−)-5,6,7,8,5',6',7',8'-1,1'-binaphthyl-2,2'-diyl phosphate] was used as a catalyst, benzaldehyde was changed into ethylmethylglyoxylate, and the reaction was carried out at room temperature for 16 hours, to obtain 2-methyl-2-ethoxycarbonyl-2,3-dihydro-4H-pyran-4-one with a yield of 39% with an optical purity of 17% ee(S).

EXAMPLE 22

Synthesis of 2-phenyl-2-ethoxycarbonyl-2,3-dihydro-4H-pyran-4-one

The same operation as in Example 11 was carried out except that the compound obtained in Example 10: scandium tris[(R)-(−)-5,6,7,8,5',6',7',8'-1,1'-binaphthyl-2,2'-diyl phosphate] was used as a catalyst, benzaldehyde was changed into ethylphenylglyoxylate, and the reaction was carried out at room temperature for 16 hours, to obtain 2-phenyl-2-ethoxycarbonyl-2,3-dihydro-4H-pyran-4-one with a yield of 44% with an optical purity of 3% ee(S).

The novel binaphthol monophosphate derivatives of the present invention can be used as a catalyst for asymmetric synthesis which can be used under practical reaction conditions and which will provide a high optical purity, and the novel binaphthol monophosphoric acid derivatives of the present invention are useful as an intermediate therefor.

Further, the pyran compounds obtained by the method of the present invention are compounds useful as an intermediate for synthesis of pharmaceutical and agricultural chemicals.

What is claimed is:

1. A binaphthol monophosphoric acid derivative of the following formula (1), (2), (3) or (4):

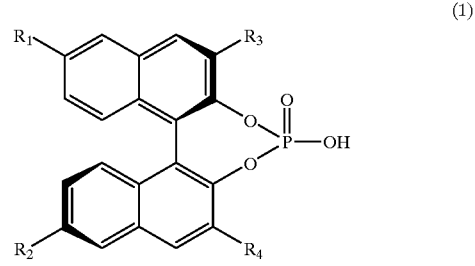

(1)

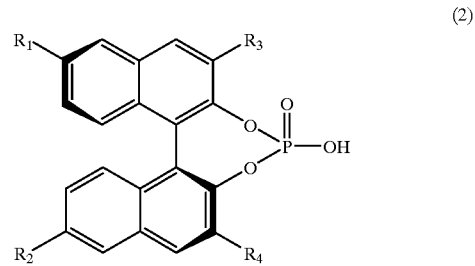

(2)

wherein each of $R_1$, $R_2$, $R_3$ and $R_4$ which are independent of one another, is hydrogen, a $C_{2-20}$ linear or branched alkenyl group, a $C_{2-20}$ linear or branched alkynyl group, a phenyl group, a phenyl group having at least one 2- to 6-positions on the phenyl ring substituted by a $C_{1-10}$ linear or branched alkyl group at the 1- to 4-carbon atom, a phenyl group having its nucleus substituted at the 1- to 4-carbon atom by a $C_2$–$C_{10}$ linear or branched alkenyl group, a phenyl group having its nucleus substituted at the 1- to 4-carbon atom by a $C_{2-10}$ linear or branched alkynyl group, a naphthyl group or a $C_{3-8}$ cycloalkyl group, provided that $R_1$ to $R_4$ are not all simultaneously hydrogen, (3)

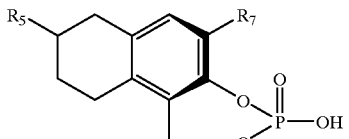

(4)

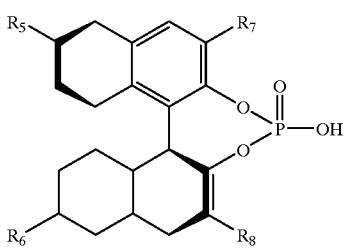

wherein each of $R_5$, $R_6$, $R_7$ and $R_8$ which are independent of one another, is hydrogen, a $C_{1-20}$ linear or branched alkyl group, a $C_{2-20}$ linear or branched alkynyl group, a phenyl group, a phenyl group having its nucleus substituted at the 1- to 4-carbon atom by a $C_{1-10}$ linear or branched alkyl group, a phenyl group having its nucleus substituted at the 1- to 4-carbon atom by a $C_{2-10}$ linear or branched alkenyl group, a phenyl group having its nucleus substituted at the 1- to 4-carbon atom by a $C_{2-10}$ linear or branched alkynyl group, a naphthyl group or a $C_{3-8}$ cycloalkyl group.

2. A binaphthol monophosphate derivative of the following formula (5), (6), (7) or (8):

(5)

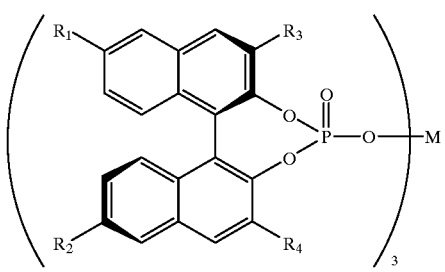

(6)

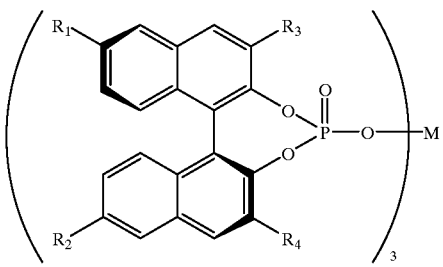

wherein each of $R_1$, $R_2$, $R_3$ and $R_4$ which are independent of one another, is hydrogen, a $C_{1-20}$ linear or branched alkyl group, a $C_{2-20}$ linear or branched alkenyl group, a $C_{2-20}$ linear or branched alkynyl group, a phenyl group, a phenyl group having its nucleus substituted at the 1- to 4-carbon atom by a $C_{1-10}$ linear or branched alkyl group, a phenyl group having its nucleus substituted at the 1- to 4-carbon atom by a $C_{2-10}$ linear or branched alkenyl group, a phenyl group having its nucleus substituted at the 1- to 4-carbon atom by a $C_{2-10}$ linear or branched alkynyl group, a naphthyl group or a $C_{3-8}$ cycloalkyl group, provided that $R_1$ to $R_4$ are not simultaneously hydrogen, and M is a metal element capable of forning a trivalent metal ion, (7)

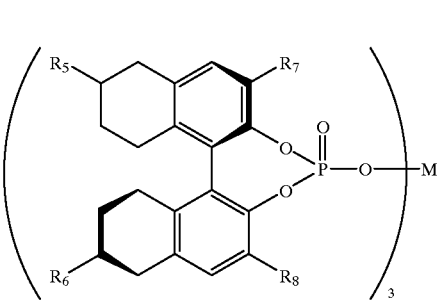

(8)

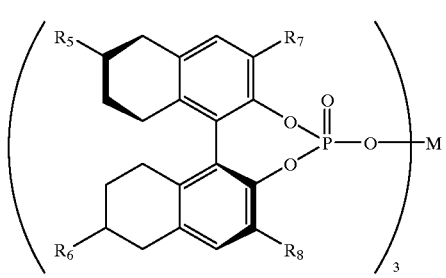

wherein each of $R_5$, $R_6$, $R_7$ and $R_8$ which are independent of one another, is hydrogen, a $C_{1-20}$ linear or branched alkyl group, a $C_{2-20}$ linear or branched alkenyl group, a $C_{2-20}$ linear or branched alkynyl group, a phenyl group, a phenyl group having its nucleus substituted at the 1- to 4-carbon atom by a $C_{1-20}$ linear or branched alkyl group, a phenyl group having its nucleus substituted at the 1- to 4-carbon atom by a $C_{2-20}$ linear or branched alkenyl group, a phenyl group having its nucleus substituted at the 1- to 4-carbon atom by a $C_{2-10}$ linear or branched alkynyl group, a naphthyl group or a $C_{3-8}$ cycloalkyl group, and M is a metal element capable of forming a trivalent metal ion.

3. A catalyst for asymmetric synthesis, which comprises the binaphthol monophosphate derivative of claim 2.

4. A process for preparing a heterocyclic compound of the following formula (9):

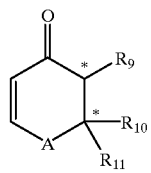

(9)

wherein the symbol * denotes an asymmetric carbon atom, each of $R_9$ and $R_{10}$ which are independent of each other, is a $C_{2-20}$ linear or branched alkyl group, a $C_{2-20}$ linear or branched alkenyl group, a $C_{2-20}$ linear or branched alkynyl group, a phenyl group, a phenyl group having its nucleus substituted at the 1- to 4-carbon atom by a $C_{1-10}$ linear or branched alkyl group, a phenyl group having its nucleus substituted at the 1- to 4-carbon atom by a $C_{2-10}$ linear or branched alkenyl group, a phenyl group having its nucleus substituted at the 1- to 4-carbon atom by a $C_{1-10}$ linear or branched alkynyl group, a phenyl group having its nucleus substituted at the 1- to 4-carbon atom by a $C_{2-10}$ linear or branched alkoxy group, a naphthyl group, a $C_{3-8}$ cycloalkyl group, a $C_{1-10}$ alkyl group having a phenyl group, or a $C_{1-10}$ alkyl group having a phenyl group having its nucleus substituted at the 1- to 4-carbon atom by a $C_{1-10}$ linear or branched alkyl group, or $R_9$ may be a hydrogen atom, $R_{11}$ is hydrogen, a $C_{1-20}$ linear or branched alkyl group, a $C_{2-20}$ linear or branched alkenyl group, a $C_{2-20}$ linear or branched alkynyl group, a phenyl group, a phenyl group having its nucleus substituted at the 1- to 4-carbon atom by a $C_{2-10}$ linear or branched alkyl group, a phenyl group having its nucleus substituted at the 1- to 4-carbon atom by a $C_{2-10}$ linear or branched alkenyl group, a phenyl group having its nucleus substituted at the 1- to 4-carbon atom by a $C_{2-10}$ linear or branched alkynyl group, a phenyl group having its nucleus substituted at the 1- to 4-carbon atom by a $C_{1-10}$ linear or branched alkoxy group, a naphthyl group, a $C_{3-8}$ cycloalkyl group, a $C_{1-10}$ alkyl group having a phenyl group, a $C_{1-10}$ alkyl group having a phenyl group having its nucleus substituted at the 1- to 4-carbon atom by a $C_{1-10}$ linear or branched alkyl group, a $C_{1-19}$ linear or branched alkylcarbonyl group, a $C_{2-19}$ linear or branched alkenylcarbonyl group, a $C_{2-19}$ linear or branched alkynylcarbonyl group, a phenylcarbonyl group, a phenylcarbonyl group having its nucleus substituted at the 1- to 4-carbon atom by a $C_{1-9}$ linear or branched alkyl group, a phenylcarbonyl group having its nucleus substituted at the 1- to 4-carbon atom by a $C_{2-9}$ linear or branched alkenyl group, a phenylcarbonyl group having its nucleus substituted at the 1- to 4-carbon atom by a $C_{2-9}$ linear or branched alkynyl group, a naphthylcarbonyl group, a $C_{3-8}$ cycloalkylcarbonyl group, a $C_{1-9}$ alkylcarbonyl group having a phenyl group, a $C_{1-9}$ alkylcarbonyl group having a phenyl group having its nucleus substituted at the 1- to 4-carbon atom by a $C_{1-9}$ linear or branched alkyl group, a $C_{1-19}$ linear or branched alkyloxycarbonyl group, a phenyloxycarbonyl group, or a phenyloxycarbonyl group having its nucleus substituted at the 1- to 4-carbon atom by a $C_{1-9}$ linear or branched alkyl group, provided that $R_{10}$ and $R_{11}$ are not the same, and A is an oxygen, nitrogen, sulfur or selenium atom;

which process comprises reacting an aldehyde or a ketone with a diene in the presence of the catalyst for asymmetric synthesis comprising the binaphthol monophosphate derivative of the following formula (5), (6), (7) or (8):

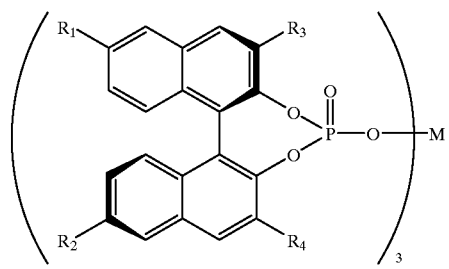

(5)

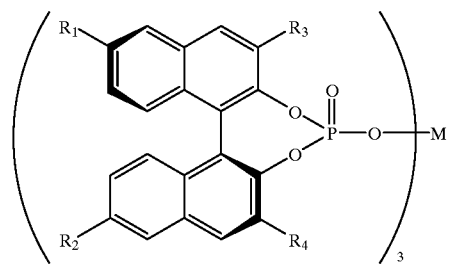

(6)

wherein each of $R_1$, $R_2$, $R_3$ and $R_4$ which are independent of one another, is hydrogen, a $C_{1-20}$ linear or branched alkyl group, a $C_{2-20}$ linear or branched alkenyl group, a $C_{2-20}$ linear or branched alkynyl group, a phenyl group, a phenyl group having its nucleus substituted at the 1- to 4-carbon atom by a $C_{1-10}$ linear or branched alkyl group, a phenyl group having its nucleus substituted at the 1- to 4-carbon atom by a $C_{2-10}$ linear or branched alkenyl group, a phenyl group having its nucleus substituted at the 1- to 4-carbon atom by a $C_{2-10}$ linear or branched alkynyl group, a naphthyl group or a $C_{3-8}$ cycloalkyl group, provided that $R_1$ to $R_4$ are not simultaneously hydrogen, and M is a metal element capable of forming a trivalent metal ion,

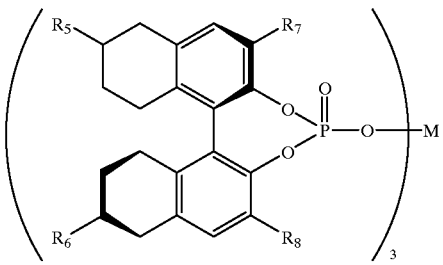

(7)

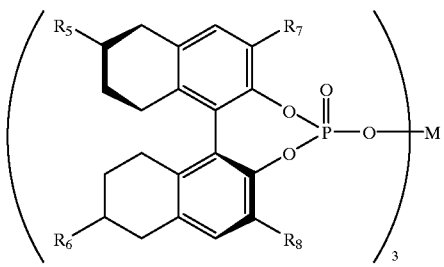

(8)

wherein each of $R_5$, $R_6$, $R_7$ and $R_8$ which are independent of one another, is hydrogen, a $C_{1-20}$ linear or branched alkyl group, a $C_{2-20}$ linear or branched alkenyl group, a $C_{2-20}$ linear or branched alkynyl group, a phenyl group, a phenyl group having its nucleus substituted at the 1- to 4-carbon atom by a $C_{1-10}$ linear or branched alkyl group, a phenyl group having its nucleus substituted at the 1- to 4-carbon atom by a $C_{2-10}$ linear or branched alkenyl group, a phenyl group having its nucleus substituted at the 1- to 4-carbon atom by a $C_{2-10}$ linear or branched alkynyl group, a naphthyl group or a $C_{3-8}$ cycloalkyl group, and M is a metal element capable of forming a trivalent metal ion.

* * * * *